United States Patent [19]

Heller et al.

[11] 4,163,536

[45] Aug. 7, 1979

[54] SUPPORT DEVICE

[75] Inventors: Rudolf Heller; Kurt Schattmaier, both of Zürich, Switzerland

[73] Assignee: Contraves AG, Zürich, Switzerland

[21] Appl. No.: 831,431

[22] Filed: Sep. 8, 1977

[30] Foreign Application Priority Data

Oct. 28, 1976 [CH] Switzerland .................. 13595/76

[51] Int. Cl.$^2$ ............................................... B68G 5/00
[52] U.S. Cl. .................................... 248/118; 248/410; 248/413
[58] Field of Search ................. 248/118, 118.1, 118.3, 248/118.5, 123, 162, 356, 410, 413

[56] References Cited

U.S. PATENT DOCUMENTS

| 316,101 | 4/1885 | White | 248/118 |
|---|---|---|---|
| 633,021 | 9/1899 | Mason | 248/413 X |
| 1,372,456 | 3/1921 | Roetter | 248/410 |
| 1,782,660 | 11/1930 | Meyer | 248/162 X |
| 1,879,865 | 9/1932 | Wright | 248/410 |
| 2,051,833 | 8/1936 | Ehrlich | 248/162 X |
| 3,929,309 | 12/1975 | De Vore | 248/118 |
| 4,018,217 | 4/1977 | Evans | 248/118.3 |

FOREIGN PATENT DOCUMENTS

| 812456 | 8/1951 | Fed. Rep. of Germany | 248/118 |
|---|---|---|---|
| 16919 | of 1914 | United Kingdom | 248/118 |

*Primary Examiner*—William H. Schultz
*Attorney, Agent, or Firm*—Werner W. Kleeman

[57] ABSTRACT

An apparatus for assisting carrying out exact hand movements, especially those performed by a surgeon during complex micro-surgical operations, comprising at least one support accommodated to the human arm or the hand. There is provided only a single upright column, one end of which is supported in a hinge joint equipped with a first brake device in order to obtain a free, braked mobility throughout a predetermined spatial region or zone with regard to the position and orientation thereof and at the other end such upright column carries the arm support. This arm support is mounted to be freely rotatable about the lengthwise axis of the upright column and is equipped with means located in the upright column for the continuous or infinite elevational adjustment of the upright column and thereby the arm support. There is also provided a second brake device for fixing the desired elevational position of the adjusted upright column and its arm support.

5 Claims, 3 Drawing Figures

SUPPORT DEVICE

BACKGROUND OF THE INVENTION

The present invention relates to a new and improved construction of device for assisting the performance of exact hand movements, in particular those carried out by a surgeon when performing time-consuming and complex micro-surgical operations, which device is of the type comprising at least one support or support member which is accommodated to the human arm or the hand.

There is already known to the art a device from German patent publication No. 2,352,026 for assisting the human arm in carrying out exact movements, for instance during micro-surgical operations, which device comprises rod members guided in appropriately structured clamping jaws and arranged laterally of the operation table, this device being elevationally adjustable and stationarily affixed to the operation table. Such device essentially comprises a slide ring secured to the upper end of the rods, this slide ring being partially open and inclinable in relation to the support surface of the operation table. Upon such slide ring there is randomly displaceable a carriage possessing two overhang arms formed thereat and directed towards the operating or work zone and the center of the slide ring, respectively. In each case a support web is arranged upon the overhang arms and at such support web there is articulated at the front region thereof a respective support element which can be pivoted through a predetermined angle and can be rocked up or down and at the same time fixed in the desired adjusted position. When performing an operation with this equipment the user must first shift the slide ring in relation to the operation table and thereafter place the carriage together with the arm-support webs in the necessary position corresponding to the work- and operation zone which is accommodated to the patient. This device is associated with the drawback that the user, namely most frequently the doctor or surgeon, is unable to correct or change, during the operation, the support elements which were adjusted prior to performing the operation, without endangering the sterility of his or her hands. Additionally, such type of devices which are stationarily fixed to the operation table have not been successful in practice due to the rather rigid elements which protrude into the operation-working field or zone and markedly limit the freedom of movement of the user.

SUMMARY OF THE INVENTION

Hence, with the foregoing in mind it is a primary object of the present invention to provide a new and improved construction of support device of the character described which is not associated with the aforementioned drawbacks and limitations of the prior art proposals.

Another and more specific object of the present invention is directed to the provision of a continuously elevationally adjustable device for supporting a human arm or hand, which, when necessary, and while retaining the requisite stability, especially also during the performance of a surgical operation, can be rocked by the user without any particular expenditure in effort or equipment into a random position which freely exposes the field or zone where the operation is to be carried out and can be freely stationarily retained in this position, and furthermore, without any difficulty with the user's arm can be again rocked back into the operation position, without during performance of these movements there occuring any contact of the sterilized parts or elements with the non-sterilized parts or elements.

Yet a further significant object of the present invention is concerned with a new and improved construction of device for assisting the performance of exact hand movements, typically but not exclusively, those carried out by a surgeon when performing delicate micro-surgical operations, which device is relatively simple in construction and design, extremely economical to manufacture, highly reliable in operation, quite easy to use, and enables the arm support of the device to be shifted into a desired position and fixedly held thereat until selecting a new position, without any great dificulty and significantly, without endangering the sterility of the hands of the user, something of importance during surgical operations.

Now in order to implement these and still further objects of the invention, which will become more readily apparent as the description proceeds, the device of this development is manifested by the features that there is provided a single upright column. In order for this upright column to possess a free, braked mobility within a predetermined region or zone with respect to its position and orientation, one end of the upright column is supported in a hinge joint or hinge means equipped with a first brake device and the other end of the upright column carries the arm support or support member. This arm support is mounted to be freely rotatable about the lengthwise axis of the upright column. Further, means are arranged in the upright column to enable continuous elevational adjustment thereof, and the elevationally adjusted position of the upright column and the arm support carried thereby can be fixed by a second brake device.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
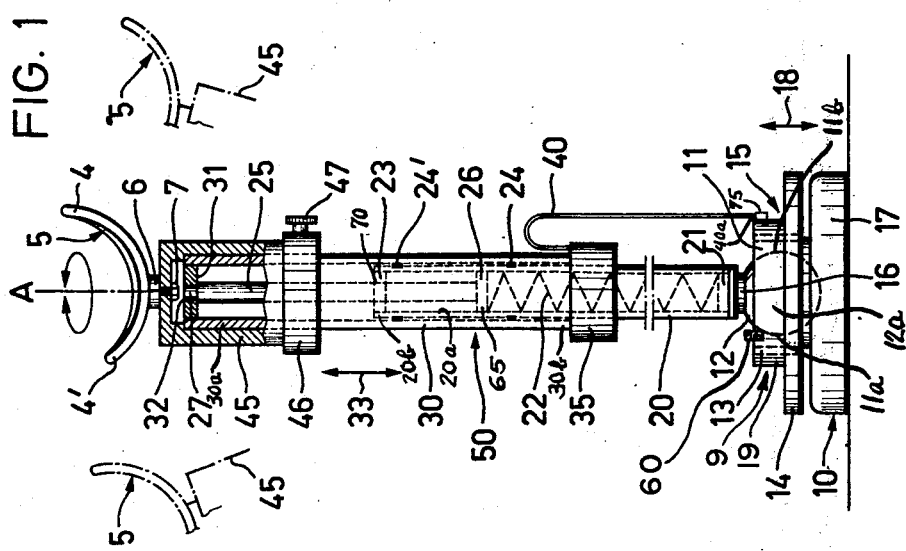
FIG. 1 is a side view, partially in section, of a freely movable and elevationally adjustable support device equipped with a support member for an arm of the user.

Describing now the drawings, in FIG. 1 there is shown in side view and partially sectional view an exemplary embodiment of an infinitely or continuously elevationally adjustable and freely movable support device, generally designated in its entirety by reference character 50. This support device 50 comprises a socket member or portion 10, an upright column structure incorporating an upright tube 20, a guide tube 30 and a further guide tube 45. Secured to the guide tube 45, as will be explained more fully hereinafter, is an arm support or support member 5 mounted to be rotatable about the lengthwise axis A of the support device 50.

The socket portion or socket 10, which is of conventional construction, essentially comprises a base plate 17 and a housing 11 which is lined with any appropriate plastic having good sliding properties. Housing 11 is structured to possess a recess or socket portion 11a in which there is received a hinge element 12 here shown in the form of a ball 12a. The hinge element 12 has the major part of its periphery freely movably mounted in the plastic-lining, generally represented by reference character 11b, of the recess or socket 11a of the housing 11, in order to thereby possess a certain degree of freedom of mobility which then can be braked with variable contact pressure by means of the schematically illustrated adjustment or setting screw 60 or other appropriate structure suitable for this purpose. The housing 11 together with the plastic-lining 11b and the adjustment screw 60 collectively form a first brake device 9 for the ball-hinge joint 12, which as will be apparent defines, in the embodiment under discussion, a ball-and-socket joint. The pivotal range or region of the support device 50 has been shown in broken lines to the left and right of FIG. 1, and this freedom of mobility of the support device is in direct correlation or relationship to the degree of freedom of movement of the hinge element 12 in the housing 11. At the freely exposed side of the hinge element 12 there is provided a flange 16, by means of which the entire socket portion 10 can be releasably connected by any suitable means, such as threading, fastening devices or other conventional structure, with the upright tube or pipe 20.

Continuing, within the upright tube 20 which is attached to the hinge element 12 there is arranged means for elevationally adjusting the position of the upright column, and specifically both of the guide tubes 30 and 45 as well as the arm support or support member 5. In the embodiment under discussion such elevationally adjusting means comprises a pressure or compression spring 22 located within the upright tube 20, this spring bearing at one end against a disc or plate member 21 which is fixedly connected with the upright tube 20 and at its other end bears against a disc or plate 26. This disc or plate 26 is movable axially to-and-fro within the upright tube 20 and is attached in any convenient fashion with a plunger or rod 25. By way of example and not limitation the disc 26 may be threaded onto the plunger or rod 25 and equally the disc 21 can be fixedly connected with the upright tube 20 by threading or in any other suitable manner. Now disc or plate 26 will be understood to possess at its outer periphery a slide ring, generally indicated by reference character 65, beneficially formed of plastic having good sliding properties and bearing against the inner wall 20a of the upright tube 20. At the upper end 20b of the upright tube 20 there is provided a further ring-shaped or annular disc or plate 23 which is likewise fixedly connected in any suitable fashion as previously explained, with such upright tube 20. This disc or plate member 23 also is equipped with a slide ring, generally indicated by reference character 70, formed of, for instance, plastic having good sliding properties and arranged at the inner diameter of such annular disc or plate 23. As evident from the showing of FIG. 1, the plunger or rod 25 piercingly extends through the annular disc or plate member 23 and thus the latter contributes to the guiding of the movement of such plunger or rod 25.

The upright tube 20 which is telescopically arranged within the guide tube 30 will be seen to be equipped at its outer periphery with at least two slide rings 24 and 24' arranged in spaced relationship from one another. These slide rings 24 and 24' are advantageously also formed of plastic possessing good sliding properties, so that the guide tube 30 is centered and guided extremely well for to-and-fro movement axially in the direction of the double-headed arrow 33. At the upper region 30a of the guide tube 30 there is arranged a disc or plate member 31 possessing an opening 32 for receiving the stepped end 27 of the plunger or rod 25 which is secured to such disc or plate member 31 by any appropriate means, for instance by threading or other equivalent structure. Now for the continuous or infinite elevational adjustment there is provided at the lower end 30b of the guide tube 30 a mechanical brake device which is arranged in a housing 35 and which brake device will be described more fully hereinafter.

Figure 3:
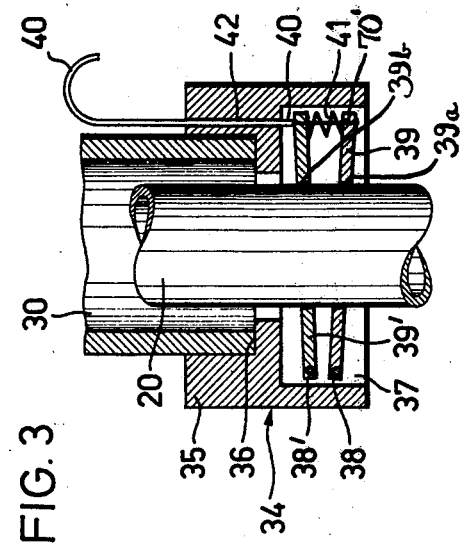
FIG. 3 is a detailed fragmentary sectional view of a brake housing for the elevational adjustment of the support device shown in FIG. 1 and equally the variant embodiment of FIG. 2.

In particular by referring to FIG. 3 there is shown on an enlarged scale this mechanical brake device which constitutes a second brake device or brake means 34. There will be recognized in greater detail the housing 35 which is fixedly connected with the guide tube 30 which protrudes upwardly from a substantially ring-shaped shoulder or projection 36. Also, there will be seen the upright tube 20 which is arranged within the hollow guide tube 30 and two annular or ring-shaped brake rings or ring members 39 and 39' which are arranged within a recess or space 37 of the housing 35 and engage about the upright tube 20, as shown. These annular brake rings or ring members 39 and 39' are arranged in superimposed space relationship with regard to one another and at one side each such brake ring is pivotably mounted at a related hinge or pivot pin 38 and 38', respectively, which is attached in any convenient fashion to the not particularly referenced wall of the housing 35. At the other oppositely situated side of such brake rings 39 and 39' there is arranged therebetween means for urging apart both of these brake rings 39 and 39'. In the embodiment under discussion the means for urging apart both of the brake rings or ring members 39 and 39' comprises at least one pressure or compression spring 41, such spring urging both such brake springs away from one another to such an extent until the inner diameter-wall portions 39a and 39b of the brake rings 39 and 39', respectively, cantingly bear at the outer diameter of the upright tube 20, with the result that the guide tube 30 is held in its position relative to the upright tube 20.

Both of the annular or ring-shaped brake rings 39 and 39' are operatively connected with one another by means of a Bowden cable 40 or other equivalent or suitable structure. This Bowden cable 40 is attached at one end, at location 70' (FIG. 3) with the lower brake ring 39 and also bears, as shown, against the top surface of the upper brake ring 39' whereas the free end 40a of such Bowden cable is guided through an opening 42 provided in the housing 35 and is secured to a foot pedal 15, as best seen by referring to FIG. 1. This foot pedal 15 essentially comprises a sleeve or sleeve member 19 surrounding the housing 11 of the socket or base portion 10 and a ring member 14 which is attached to such sleeve or sleeve member 19. As best seen by referring to the showing of FIG. 1, the free end 40a of the Bowden cable is connected at location 75 with the sleeve 19. In order to obtain an optimum guiding of the elements 19 and 14 in the direction of the double-headed arrow 18, there is preferably arranged between the housing 11 and the sleeve 19 a bushing 13 formed of plastic, such as for instance, polytetrafluoroethylene (PTFE), having good sliding properties, and also known under the well known mark "TEFLON." In fact this plastic may be used for those plastic components of the device heretofore described, whenever good sliding properties are desired.

Now for the elevational adjustment of the support device 50 the foot pedal 15 which is connected by the Bowden cable 40 with the spring 41, is moved downwardly for instance by the action of the foot of the user, against the spring force, in the corresponding direction of the double-headed arrow 18, and consequently, the break or braking rings 39 and 39', are no longer in braking engagement with the upright tube 20. Due to this downward movement of the foot pedal 15 and the release of the second brake means or device 34, it is possible to optionally adjust the height of the support member 5 in the direction of the double-headed arrow 33, and upon release of the foot pedal 15 the brake rings 39 and 39', under the force of the spring 41, are immediately again brought into braking engagement with the outer periphery of the upright tube 20, and thus, there can be easily fixed the selected height of the support device 50.

In the illustrated embodiment the elevational adjustment of the support member or support 5 is accomplished by means of the pressure or compression spring 22, in other words mechanically, but it is to be expressly understood that the possibility is readily available of achieving this result in a different way, for instance by installing conventional hydraulically or pneumatically operating lifting devices in the support device.

It is here mentioned that at the upper end of the support device 50 there is provided a further, detachable guide tube 45 which is carried by the guide tube 30. This guide tube 45 can be axially shifted upon the guide tube 30 and locked fixedly in position by means of an adjustment or setting ring 46 having an adjustment or setting screw 47 or equivalent structure. Now upon the guide tube 45 there is secured by means of a screw 7 or any other suitable attachment means the support member or support 5 which is preferably accommodated anatomically to the human arm or hand. In order to provide a faultless and easy use of the equipment—insertion and removal of the arm or the hand into and out of the support member 5—this support member 5 which is preferably formed of a tubular section i.e., a section or part of a tubular member having the side portions 4 and 4', is constructed in such a manner that the one side portion 4' possesses a lower height than the other side portion 4. In this way there is beneficially achieved the result that the arm or the hand of the user is well supported at the side portion 4 of the support member 5 and on the other hand can be easily removed out of the support member 5, possessing a substantially bowl-like configuration, at the other side thereof, namely at the region of the side portion 4'. This support member 5 is furthermore rotatably mounted about the lengthwise axis of the support device 50 which is constructed as an upright column or column arrangement, and an additional sliding or slide disc 6 is provided between the support member 5 and the upper edge of the guide tube 45.

Figure 2:
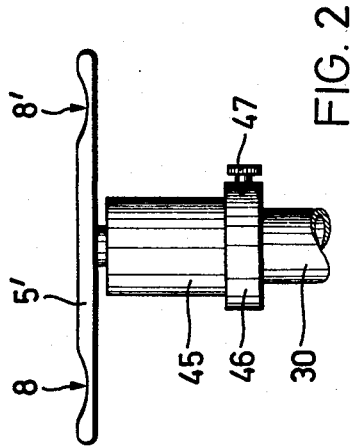
FIG. 2 is a fragmentary view of a variant modification of the upper portion of the support device, here shown equipped with a support member for two arms.

Finally, in the showing of FIG. 2 there is portrayed a variant construction of arm support 5' which is here equipped with two anatomically constructed recesses or depression 8 and 8' for receiving both arms of the user. The support member 5 of the support device 50 shown in FIG. 1 can be easily exchanged for the support member 5' of the modified arrangement of FIG. 2. The guide tube 45 together with the support member 5 or 5', as the case may be, is detachably connected, as previously explained, with the support device 50 in order to be able to carry out easier sterilization of such components.

While there are shown and described present preferred embodiments of the invention, it is to be distinctly understood that the invention is not limited thereto, but may be otherwise variously embodied and practiced within the scope of the following claims.

Accordingly, what we claim is:

1. A device for assisting in the performance of exact hand movements, especially those of a surgeon when carrying out delicate micro-surgical operations, which device comprises:

at least one support member accommodated to the human arm or hand;

a single upright column means for carrying said support member;

said single upright column means having opposed end regions;

means including a hinge arrangement provided at one end region of said single upright column means for enabling a desired freedom of movement of said column means throughout a predetermined spatial region;

a first brake device cooperating with said hinge means for freely brakingly fixing the adjusted position of the column means;

means for securing the support member to the other end region of said column means and for enabling free rotational movement of said support member about the lengthwise axis of said column means;

means arranged within said column means for the continuous elevational adjustment of said column means; and a second brake device for fixing the elevationally adjusted position of the column means and thus the support member.

said second brake device comprising:

a housing provided with recess means;

two annular brake ring members arranged in said recess means and engaging about said upright tube;

means for hingedly connecting the brake ring members at one side with said housing;

a compression spring arranged between and at the other side of said brake ring member; and a Bowden cable for actuating said second brake device.

2. A device for assisting in the performance of exact hand movements, especially those of a surgeon when carrying out delicate micro-surgical operations, which device comprises:

at least one support member accommodated to the human arm or hand;

a single upright column means for carrying said support member;

said single upright column means having opposed end regions;

means including a hinge arrangement provided at one end region of said single upright column means for enabling a desired freedom of movement of said column means throughout a predetermined spatial region;

a first brake device cooperating with said hinge means for freely brakingly fixing the adjusted position of the column means;

means for securing the support member to the other end region of said column means and for enabling free rotational movement of said support member about the lengthwise axis of said column means;

means arranged within said column means for the continuous elevational adjustment of said column means;

a second brake device for fixing the elevationally adjusted position of the column means and thus the support member;

said support member being carried by said other end region of said column means by means of a guide tube;

means for attaching said support member to said guide tube;

said column means including a guide tube member; and said guide tube being supported upon said guide tube member and elevationally displaceable with respect thereto and fixable in position by means of an adjustment ring.

3. The device as defined in claim 2, wherein:
said upright column means comprises:
an upright tube;
a guide tube carrying the support member;
compression spring means for biasing said guide tube and constituting at least part of the means for the continuous elevational adjustment of said column means;
said second brake device operatively co-operating with said upright tube; and
said guide tube, upon release of said second brake device, being selectively continuously elevationally adjustable in position and then fixable by said second brake device in said adjusted elevational position.

4. The device as defined in claim 2, wherein:
said support member comprises an anatomically configured, substantially bowl-shaped tube section having two side portions.

5. The device as defined in claim 4, wherein:
one of said side portions possesses a smaller side height than the other side portion.

* * * * *